US008063188B2

(12) United States Patent
Sayers et al.

(10) Patent No.: US 8,063,188 B2
(45) Date of Patent: Nov. 22, 2011

(54) ANTI-MYOSTATIN ANTIBODIES

(75) Inventors: Robert Owen Sayers, Encinitas, CA (US); Lihua Huang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 432 days.

(21) Appl. No.: 12/376,390

(22) PCT Filed: Aug. 23, 2007

(86) PCT No.: PCT/US2007/076604
§ 371 (c)(1),
(2), (4) Date: Feb. 4, 2009

(87) PCT Pub. No.: WO2008/030706
PCT Pub. Date: Mar. 13, 2008

(65) Prior Publication Data
US 2010/0166764 A1    Jul. 1, 2010

Related U.S. Application Data

(60) Provisional application No. 60/824,498, filed on Sep. 5, 2006.

(51) Int. Cl.
*C07K 16/24* (2006.01)
*C07K 16/00* (2006.01)
*A61K 39/395* (2006.01)

(52) U.S. Cl. ............. 530/388.23; 530/387.1; 530/388.1; 530/387.3; 424/130.1; 424/133.1; 424/141.1; 424/145.1

(58) Field of Classification Search .................. None
See application file for complete search history.

(56) References Cited

U.S. PATENT DOCUMENTS

| | | | |
|---|---|---|---|
| 5,639,638 A | 6/1997 | Wozney et al. |
| 5,700,911 A | 12/1997 | Wozney et al. |
| 5,827,733 A | 10/1998 | Lee et al. |
| 5,914,234 A | 6/1999 | Lee et al. |
| 6,096,506 A | 8/2000 | Lee et al. |
| 6,340,668 B1 | 1/2002 | Celeste et al. |
| 6,368,597 B1 | 4/2002 | Strassmann et al. |
| 6,437,111 B1 | 8/2002 | Wozney et al. |
| 6,468,535 B1 | 10/2002 | Lee et al. |
| 6,500,664 B1 | 12/2002 | Lee et al. |
| 6,517,835 B2 | 2/2003 | Lee et al. |
| 6,656,475 B1 | 12/2003 | Lee et al. |
| 6,696,260 B1 | 2/2004 | Lee et al. |
| 6,858,208 B2 | 2/2005 | Lee et al. |
| 7,175,997 B2 | 2/2007 | Wozney et al. |
| 7,179,884 B2 | 2/2007 | Lee et al. |
| 7,261,893 B2 | 8/2007 | Veldman et al. |
| 7,320,789 B2 | 1/2008 | Dunham et al. |
| 7,371,726 B2 | 5/2008 | Junker et al. |
| 7,511,012 B2 | 3/2009 | Han et al. |
| 7,534,432 B2 | 5/2009 | Lee et al. |
| 7,585,648 B2 | 9/2009 | Junker et al. |
| 2002/0150577 A1 | 10/2002 | Lee et al. |
| 2003/0138422 A1 | 7/2003 | Aghajanian et al. |
| 2004/0142382 A1 | 7/2004 | Veldman et al. |
| 2004/0181033 A1 | 9/2004 | Han et al. |
| 2005/0014733 A1 | 1/2005 | Whittemore et al. |
| 2005/0043232 A1 | 2/2005 | Lee et al. |
| 2005/0143306 A1 | 6/2005 | Junker et al. |
| 2006/0216279 A1 | 9/2006 | Glass et al. |
| 2006/0240487 A1 | 10/2006 | Nowak et al. |
| 2006/0263354 A1 | 11/2006 | Chin et al. |
| 2007/0087000 A1 | 4/2007 | Walsh et al. |
| 2007/0149458 A1 | 6/2007 | Han et al. |
| 2007/0178097 A1 | 8/2007 | Presta |
| 2007/0190056 A1 | 8/2007 | Kambadur et al. |
| 2008/0051328 A1 | 2/2008 | Sharma et al. |
| 2008/0187543 A1 | 8/2008 | Kambadur et al. |
| 2008/0299126 A1 | 12/2008 | Han et al. |
| 2009/0017045 A1 | 1/2009 | Lee et al. |
| 2009/0017522 A1 | 1/2009 | Lee et al. |
| 2009/0136481 A1 | 5/2009 | Kambadur et al. |
| 2009/0215671 A1 | 8/2009 | Calof et al. |
| 2009/0220491 A1 | 9/2009 | Han et al. |
| 2009/0311282 A1 | 12/2009 | Junker et al. |

FOREIGN PATENT DOCUMENTS

| | | |
|---|---|---|
| EP | 1333035 | 8/2003 |
| EP | 0690873 B1 | 11/2003 |
| EP | 0776337 B1 | 9/2005 |
| GB | 2 333 706 A | 4/1999 |
| WO | WO 94/21681 | 9/1994 |
| WO | WO 94/26892 | 11/1994 |
| WO | WO 96/01845 | 1/1996 |
| WO | 9835019 | 8/1998 |
| WO | WO 99/06559 | 2/1999 |
| WO | WO 99/24058 | 5/1999 |
| WO | WO 99/40181 | 8/1999 |
| WO | WO 99/42573 | 8/1999 |
| WO | WO 99/56768 | 11/1999 |
| WO | WO 00/43781 | 7/2000 |
| WO | WO 02/09641 | 2/2002 |

(Continued)

OTHER PUBLICATIONS

Wagner et al. (Annals of Neurology 2008, 63:561-571).*
U.S. Appl. No. 12/066,838.
Ashmore, et al., "Comparative Aspects of Muscle Fiber Types in Fetuses of the Normal and 'Double-Muscled' Cattle," *Growth* 38:501-506 (1974).
Bogdanovich, et al., "Functional Improvement of Dystrophic Muscle by Myostatin Blockade," *Nature* 420:418-421 (2002).
Bogdanovich, et al., "Therapeutics for Duchenne Muscular Dystrophy: Current Approaches and Future Directions," *J. Mol. Med.* 82:102-115 (2004).
Gamer, et al., "Gdf11 is a Negative Regulator of Chondrogenesis and Myogenesis in the Developing Chick Limb," *Dev. Biol.* 229:407-420 (2001).

(Continued)

Primary Examiner — Sharon Wen
(74) Attorney, Agent, or Firm — Gregory A. Cox

(57) ABSTRACT

Monoclonal anti-myostatin antibodies that preferentially bind myostatin over GDF-11, have strong binding affinity to myostatin and are resistant to chemical degradation. The antibodies of the invention are useful for increasing muscle mass, increasing bone density, or for the treatment or prevention of various disorders in mammalian and avian species.

14 Claims, 5 Drawing Sheets

FOREIGN PATENT DOCUMENTS

| WO | WO 02/10214 | 2/2002 |
|---|---|---|
| WO | WO 03/027248 | 4/2003 |
| WO | WO 2004/037861 | 5/2004 |
| WO | WO 2004/058988 | 7/2004 |
| WO | WO 2004/108157 | 12/2004 |
| WO | WO 2005/066204 | 7/2005 |
| WO | WO 2005/094446 | 10/2005 |
| WO | WO 2006/020884 | 2/2006 |
| WO | WO 2006/116269 | 11/2006 |
| WO | WO 2007/024535 | 3/2007 |
| WO | WO 2007/047112 | 4/2007 |
| WO | WO 2007/067616 | 6/2007 |
| WO | 2008109167 | 9/2008 |

OTHER PUBLICATIONS

Gamer, et al., "A Novel BMP Expressed in Developing Mouse Limb, Spinal Cord, and Tail Bud Is a Potent Mesoderm Inducer in *Xenopus* Embryos," *Dev. Biol.* 208:222-232 (1999).

Gonzalez-Cadavid, et al., "Organization of the Human Myostatin Gene and Expression in Healthy Men and HIV-Infected Men With Muscle Wasting," *PNAS* 95:14938-14943 (1998).

Gonzales-Cadavid, et al., "Role of Myostatin in Metabolism," *Curr. Opin. Clin. Nutr. Metab. Care* 7:451-457 (2004).

Grobet, et al., "A Deletion in the Bovine Myostatin Gene Causes the Double-Muscled Phenotype in Cattle," *Nature Genet.* 17:71-74 (1997).

Hamrick, et al., "Femoral Morphology and Cross-Sectional Geometry of Adult Myostatin-Deficient Mice," *Bone* 27:343-349 (2000).

Hamrick, et al., "Bone Mineral Content and Density in the Humerus of Adult Myostatin-Deficient Mice," *Calcif. Tissue Int.* 71(1):63-68 (2002).

Hill, et al., "The Myostatin Propeptide and the Follistatin-Related Gene Are Inhibitory Binding Proteins of Myostatin in Normal Scrum," *J. Biol. Chem.* 277:40735-40741 (2002).

Hill, et al., "Regulation of Myostatin in Vivo by Growth and Differentiation Factor-Associated Serum Protein-1: A Novel Protein with Protease Inhibitor and Follistatin Domains," *Mol. Endocrinol.* 17:1144-1154 (2003).

Hoodless, et al., "Mechanisms and Function of Signaling by the TGFβ Superfamily," *Current Topics in Microbiology and Immunology* pp. 236-272 (1998).

Huet, et al., "Skeletal Muscle Cell Hypertrophy Induced by Inhibitors of Metalloproteases; Myostatin as a Potential Mediator," *Am. J. Physiol. Cell. Physiol.* 281:C1624-C1634 (2001).

Jiang, et al., "Characterization and Identification of the Inhibitory Domain of GDF-8 Propeptide," *Biochem. Biophys. Res. Commun.* 315:525-531 (2004).

Kambadur, et al., "Mutations in *Myostatin* (GDF8) In Double-Muscled Belgian Blue and Piedmontese Cattle," *Genome Res.* 7:910-915 (1997).

Kim, et al., "Inhibition of Preadipocyte Differentiation by Myostatin Treatment in 3T3-L1 Cultures," *Biochem. Biophys. Res. Comm.*, 281:902-906 (2001).

Kingsley, D.M., "The TGFβ Superfamily: New Members, New Receptors, and New Genetic Tests of Function in Different Organisms," *Genes & Devel.* 8:133-146 (1994).

Kirk, et al., "Myostatin Regulation During Skeletal Muscle Regeneration," *J. Cell. Physiol.*, 184:356-363 (2000).

Lang, et al., "Regulation of Myostatin by Glucocorticoids After Thermal Injury," *FASEB J.* 15:1807-1809 (2001).

Lee, et al., "Regulation of Myostatin Activity and Muscle Growth," *PNAS* 98:9306-9311 (2001).

Li, et al., "Elimination of Myostatin Does Not Combat Muscular Dystophy in dy Mice but Increases Postnatal Lethality," *AJP.* 166 (2) 491-497, 2005.

Lin, et al., "Myostatin Knockout in Mice Increases Myogenesis and Decreases Adipogenesis," *Biochem. Biophys. Res. Comm.*, 291:701-706 (2002).

Massagué, J., "The Transforming Growth Factor-β Family," *Ann. Rev. Cell Biol.* 6:597-641 (1990).

McPherron, et al., "Double Muscling in Cattle Due to Mutations in the Myostatin Gene," *PNAS* 94:12457-12461 (1997).

McPherron, et al., "Regulation of Skeletal Muscle Mass in Mice by a New TGF-β Superfamily Member," *Nature* 387:83-90 (1997).

McPherron, et al., "Suppression of Body Fat Accumulation in Myostatin-Deficient Mice," *J. Clin. Invest.* 109:595-601 (2002).

Muscaritoli, et al., "Therapy of Muscle Wasting in Cancer: What Is the Future?" *Curr. Opin. Clin. Nutr. Metab. Care*, 7:459-466 (2004).

Nakashima, et al., "Expression of Growth/Differentiation Factor 11, A New Member of the BMP/TGF β Superfamily During Mouse Embryogenesis," *Mech. Dev.* 80:185-189 (1999).

Reardon, et al., "Myostatin, Insulin-Like Growth Factor-1, and Leukemia Inhibitory Factor mRNAs Are Upregulated in Chronic Human Disuse Muscle Atrophy," *Muscle Nerve*, 24:893-899 (2001).

Rios, et al., "Myostatin Is An Inhibitor of Myogenic Differentiation," *Am. J. Physiol. Cell Physiol.*, 282: C993-C999 (2002).

Roth, et al., "Myostatin: A Therapeutic Target for Skeletal Muscle Wasting," *Curr. Opin. Clin. Nutr. Metab. Care*, 7:259-263 (2004).

Sharma, et al., "Myostatin, a Transforming Growth Factor-β Superfamily Member, Is Expressed in Heart Muscle and Is Upregulated in Cardiomyocytes After Infarct," *J. Cell. Physiol.*, 180:1-9 (1999).

Swatland, et al., "Fetal Development of the Double Muscled Condition in Cattle," *J. Animal Sci.* 38:752-757 (1974).

Thies, et al., "GDF-8 Propeptide Binds to GDF-8 and Antagonizes Biological Activity by Inhibiting GDF-8 Receptor Binding," *Growth Factors* 18:251-259 (2001).

Thomas, et al., "Myostatin, a Negative Regulator of Muscle Growth, Functions by Inhibiting Myoblast Proliferation," *J. Biol. Chem.*, 275 (51) 40235-40243 (2000).

Tseng, et al., "Regenerated mdx Mouse Skeletal Muscle Shows Differential mRNA Expression," *J. Appl. Physiol.* 93:537-545 (2002).

Tsuchida, et al., "Identification and Characterization of a Novel Follistatin-like Protein as a Binding Protein for the TGF-β Family," *J. Biol. Chem.* 275:40788-40796 (2000).

Wagner, et al., "Loss of Myostatin Attenuates Severity of Muscular Dystrophy in *mdx* Mice," *Ann. Neurol.* 52:832-836 (2002).

Wakefield, et al., "Latent Transforming Growth Factor- β From Human Platelets," *J. Biol. Chem.* 263:7646-7654 (1988).

Whittemore, et al., "Inhibition of Myostatin in Adult Mice Increases Skeletal Muscle Mass and Strength," *Biochem. Biophys. Res. Comm.* 300:965-971 (2003).

Zhu, et al., "Dominant Negative Myostatin Produces Hypertrophy Without Hyperplasia in Muscle," *FEBS Letters* 474:71-75 (2000).

Zimmers, et al., "Induction of Cachexia in Mice by Systematically Administered Myostatin," *Science* 296:1486-1488 (2002).

Tchistiakova, L., "Anti-Myostatin Antibody for Treatment of Muscle Wasting Diseases," Antibody Therapeutics Meeting, San Diego, CA, Dec. 7, 2005.

* cited by examiner

FIG. 1

A.  Myostatin: GDF-11 Homology

```
Myostatin   DFGLDCDEHSTESRCCRYPLTVDFEAFGWDWIIAPKRYK
GDF-11      NLGLDCDEHSSESRCCRYPLTVDFEAFGWDWIIAPKRYK Myostatin   ANYCSGECEFVFLQKYPHTHLVHQANPRGSAGPCCTPTK
GDF-11      ANYCSGQCEYMFMQKYPHTHLVQQANPRGSAGPCCTPTK Myostatin   MSPINMLYFNGKEQIIYGKIPAMVVDRCGCS     (SEQ ID NO:1)
GDF-11      MSPINMLYFNDKQQIIYGKIPGMVVDRCGCS     (SEQ ID NO:2)
```

B.  Antigenic epitopes of human myostatin

```
ANYCSGECEFVFLQKYPHTHLVHQA    (SEQ ID NO: 29)
CSGECEFVFLQKYPH              (SEQ ID NO: 30)
GECEFVFLQKYPHTH              (SEQ ID NO: 31)
```

FIG. 2

Light Chain

A.

510C2 (SEQ ID NO: 3)
DIQMTQSPSSLSASVGDRVTITCSASSSISYMHWYQQKPGKAPKLLIYDTSKLARGVPSRFSGSGSGTDFT
LTISSLQPEDFATYYCQQWYRNPLTFGGGTKVEIK

510C2NH (SEQ ID NO: 4)
DIQMTQSPSSLSASVGDRVTITCSASSSISYMHWYQQKPGKAPKLLIYDTSKLARGVPSRFSGSGSGTDFT
LTISSLQPEDFATYYCQQWYRHPLTFGGGTKVEIK

510C2NS (SEQ ID NO: 5)
DIQMTQSPSSLSASVGDRVTITCSASSSISYMHWYQQKPGKAPKLLIYDTSKLARGVPSRFSGSGSGTDFT
LTISSLQPEDFATYYCQQWYRSPLTFGGGTKVEIK

510C2NT (SEQ ID NO: 6)
DIQMTQSPSSLSASVGDRVTITCSASSSISYMHWYQQKPGKAPKLLIYDTSKLARGVPSRFSGSGSGTDFT
LTISSLQPEDFATYYCQQWYRTPLTFGGGTKVEIK

510C2NA (SEQ ID NO: 7)
DIQMTQSPSSLSASVGDRVTITCSASSSISYMHWYQQKPGKAPKLLIYDTSKLARGVPSRFSGSGSGTDFT
LTISSLQPEDFATYYCQQWYRAPLTFGGGTKVEIK

C12  (SEQ ID NO: 8)
DIQMTQSPSSLSASVGDRVTITCSASSSISYMHWYQQKPGKAPKLLIYDTSKLARGVPSRFSGSGSGTDFT
LTISSLQPEDFATYYCQQWYLNPLTFGGGTKVEIK

C12NH  (SEQ ID NO: 9)
DIQMTQSPSSLSASVGDRVTITCSASSSISYMHWYQQKPGKAPKLLIYDTSKLARGVPSRFSGSGSGTDFT
LTISSLQPEDFATYYCQQWYLHPLTFGGGTKVEIK

C12NR  (SEQ ID NO: 10)
DIQMTQSPSSLSASVGDRVTITCSASSSISYMHWYQQKPGKAPKLLIYDTSKLARGVPSRFSGSGSGTDFT
LTISSLQPEDFATYYCQQWYLRPLTFGGGTKVEIK

Heavy Chain

B.

510C2, 510C2NH, 510C2NS, 510C2NT and 510C2NA    (SEQ ID NO: 11)
QVTLRESGPALVKPTQTLTLTCTFSGFSLRKVGRSVSWIRQPPGKALEWLA**HIYWDDDKRYNPS
LRNRLTISKDTSKNQVVLTMTNMDPVDTATYYCARRAITTVIGGGTFDY**WGQGTTVTVSS C12, C12NH and C12NR  (SEQ ID NO: 12)
QLQLQESGPGLVKPSETLSLTCTVSGFSLRKVGSSVSWIRQPPGKGLEWIG**HIYWDDDKRLNPS
LRNRVTISVDTSKNQFSLKLSSVTAADTAVYYCARRAITTVIGGGTFDL**WGQGTLVTVSS

| Name | CDRL1 | CDRL2 | CDRL3 |
|---|---|---|---|
| 510C2 | SASSSISYMH (SEQ ID NO:13) | DTSKLAR (SEQ ID NO:14) | QQWYRNPLT (SEQ ID NO: 15) |
| 510C2NH | SASSSISYMH (SEQ ID NO:13) | DTSKLAR (SEQ ID NO:14) | QQWYRHPLT (SEQ ID NO: 16) |
| 510C2NS | SASSSISYMH (SEQ ID NO:13) | DTSKLAR (SEQ ID NO:14) | QQWYRSPLT (SEQ ID NO: 17) |
| 510C2NT | SASSSISYMH (SEQ ID NO:13) | DTSKLAR (SEQ ID NO:14) | QQWYRTPLT (SEQ ID NO: 18) |
| 510C2NA | SASSSISYMH (SEQ ID NO:13) | DTSKLAR (SEQ ID NO:14) | QQWYRAPLT (SEQ ID NO: 19) |
| C12 | SASSSISYMH (SEQ ID NO:13) | DTSKLAR (SEQ ID NO:14) | QQWYLNPLT (SEQ ID NO: 20) |
| C12NH | SASSSISYMH (SEQ ID NO:13) | DTSKLAR (SEQ ID NO:14) | QQWYLHPLT (SEQ ID NO: 21) |
| C12NR | SASSSISYMH (SEQ ID NO:13) | DTSKLAR (SEQ ID NO:14) | QQWYLRPLT (SEQ ID NO: 22) |

B.

| Name | CDRH1 | CDRH2 | CDRH3 |
|---|---|---|---|
| 510C2 | GFSLRKVGRSVS (SEQ ID NO: 23) | HIYWDDDKRYNPSLRN (SEQ ID NO: 25) | RAITTVIGGGTFDY (SEQ ID NO:27) |
| 510C2NH | GFSLRKVGRSVS (SEQ ID NO: 23) | HIYWDDDKRYNPSLRN (SEQ ID NO: 25) | RAITTVIGGGTFDY (SEQ ID NO: 27) |
| 510C2NS | GFSLRKVGRSVS (SEQ ID NO: 23) | HIYWDDDKRYNPSLRN (SEQ ID NO: 25) | RAITTVIGGGTFDY (SEQ ID NO: 27) |
| 510C2NT | GFSLRKVGRSVS (SEQ ID NO: 23) | HIYWDDDKRYNPSLRN (SEQ ID NO: 25) | RAITTVIGGGTFDY (SEQ ID NO: 27) |
| 510C2NA | GFSLRKVGRSVS (SEQ ID NO: 23) | HIYWDDDKRYNPSLRN (SEQ ID NO: 25) | RAITTVIGGGTFDY (SEQ ID NO:27) |
| C12 | GFSLRKVGSSVS (SEQ ID NO: 24) | HIYWDDDKRLNPSLRN (SEQ ID NO: 26) | RAITTVIGGGTFDL (SEQ ID NO: 28) |
| C12NH | GFSLRKVGSSVS (SEQ ID NO: 24) | HIYWDDDKRLNPSLRN (SEQ ID NO: 26) | RAITTVIGGGTFDL (SEQ ID NO: 28) |
| C12NR | GFSLRKVGSSVS (SEQ ID NO: 24) | HIYWDDDKRLNPSLRN (SEQ ID NO: 26) | RAITTVIGGGTFDL (SEQ ID NO: 28) |

Fig. 4

N93H-C12-Light Chain:
DIQMTQSPSSLSASVGDRVTITCSASSSISYMHWYQQKPGKAPKLLIYDTSKLARGVPSRFSGSGSGTDFT
LTISSLQPEDFATYYCQQWYLHPLTFGGGTKVEIKRTVAAPSVFIFPPSDEQLKSGTASVVCLLNNFYPRE
AKVQWKVDNALQSGNSQESVTEQDSKDSTYSLSSTLTLSKADYEKHKVYACEVTHQGLSSPVTKSFNRGEC
(SEQ ID NO: 32)

N93H-C12-Heavy Chain:
QLQLQESGPGLVKPSETLSLTCTVSGFSLRKVGSSVSWIRQPPGKGLEWIGHIYWDDDKRLNPSLRNRVTI
SVDTSKNQFSLKLSSVTAADTAVYYCARRAITTVIGGGTFDLWGQGTLVTVSSASTKGPSVFPLAPCSRST
SESTAALGCLVKDYFPEPVTVSWNSGALTSGVHTFPAVLQSSGLYSLSSVVTVPSSSLGTKTYTCNVDHKP
SNTKVDKRVESKYGPPCPPCPAPEFLGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPSSIEKTISKAKGQPREPQVYTL
PPSQEEMTKNQVSLTCLVKGFYPSDIAVEWESNGQPENNYKTTPPVLDSDGSFFLYSRLTVDKSRWQEGNV
FSCSVMHEALHNHYTQKSLSLSLG(SEQ ID NO: 33)

FIG. 5
A.
B.
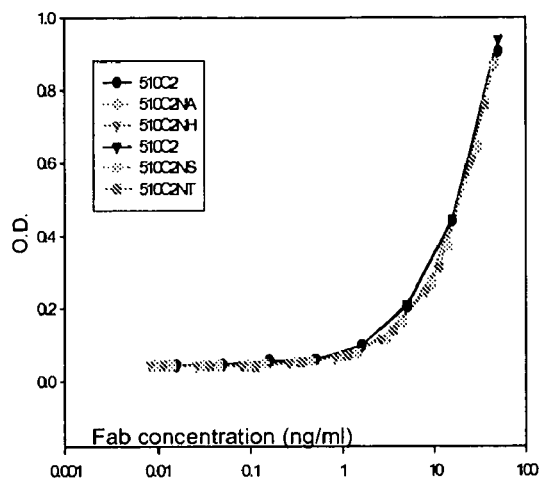
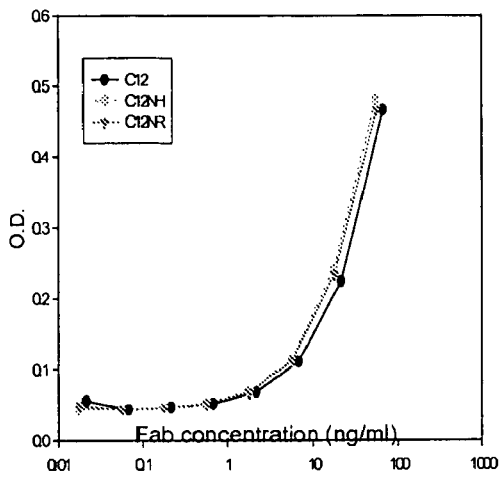

SEQUENCE LISTING

<160> NUMBER OF SEQ IDS: 36

<210> SEQ ID NO 1
<211> LENGTH: 109
<212> TYPE: PRT
<213> ORGANISM: Homo sapiens

<400> SEQUENCE: 1

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 2
<211> LENGTH: 109
<212> TYPE: PRT
<213> ORGANISM: Homo sapiens

<400> SEQUENCE: 2

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 3
<211> LENGTH: 106
<212> TYPE: PRT
<213> ORGANISM: Artificial
<220> FEATURE:
<223> OTHER INFORMATION: synthetic construct

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

```
Asp Thr Ser Lys Leu Ala Arg Gly Val Pro Ser Arg Phe Ser Gly Ser
        50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Tyr Arg Asn Pro Leu Thr
                 85                  90                  95

Phe Gly Gly Gly Thr Lys Val Glu Ile Lys
            100                 105

<210> SEQ ID NO 4
<211> LENGTH: 106
<212> TYPE: PRT
<213> ORGANISM: Artificial
<220> FEATURE:
<223> OTHER INFORMATION: synthetic construct

<400> SEQUENCE: 4

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Ile Ser Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Arg Gly Val Pro Ser Arg Phe Ser Gly Ser
        50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Tyr Arg His Pro Leu Thr
                 85                  90                  95

Phe Gly Gly Gly Thr Lys Val Glu Ile Lys
            100                 105

<210> SEQ ID NO 5
<211> LENGTH: 106
<212> TYPE: PRT
<213> ORGANISM: Artificial
<220> FEATURE:
<223> OTHER INFORMATION: synthetic construct

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Ile Ser Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Arg Gly Val Pro Ser Arg Phe Ser Gly Ser
        50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Tyr Arg Ser Pro Leu Thr
                 85                  90                  95

Phe Gly Gly Gly Thr Lys Val Glu Ile Lys
            100                 105

<210> SEQ ID NO 6
<211> LENGTH: 106
<212> TYPE: PRT
<213> ORGANISM: Artificial
```

```
<220> FEATURE:
<223> OTHER INFORMATION: synthetic construct

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ile Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Arg Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Arg Thr Pro Leu Thr
                85                  90                  95

Phe Gly Gly Gly Thr Lys Val Glu Ile Lys
            100                 105

<210> SEQ ID NO 7
<211> LENGTH: 106
<212> TYPE: PRT
<213> ORGANISM: Artificial
<220> FEATURE:
<223> OTHER INFORMATION: synthetic construct

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ile Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Arg Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Arg Ala Pro Leu Thr
                85                  90                  95

Phe Gly Gly Gly Thr Lys Val Glu Ile Lys
            100                 105

<210> SEQ ID NO 8
<211> LENGTH: 106
<212> TYPE: PRT
<213> ORGANISM: Artificial
<220> FEATURE:
<223> OTHER INFORMATION: synthetic construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ile Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Arg Gly Val Pro Ser Arg Phe Ser Gly Ser
    50                  55                  60

Gly Ser Gly Thr Asp Phe Thr Leu Thr Ile Ser Ser Leu Gln Pro Glu
```

```
65                  70                  75                  80
Asp Phe Ala Thr Tyr Tyr Cys Gln Gln Trp Tyr Leu Asn Pro Leu Thr
                85                  90                  95

Phe Gly Gly Gly Thr Lys Val Glu Ile Lys
            100                 105
```

<210> SEQ ID NO 9
<211> LENGTH: 106
<212> TYPE: PRT
<213> ORGANISM: Artificial
<220> FEATURE:
<223> OTHER INFORMATION: synthetic construct

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Arg Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Leu His Pro Leu Thr
                85                  90                  95

Phe Gly Gly Gly Thr Lys Val Glu Ile Lys
            100                 105
```

<210> SEQ ID NO 10
<211> LENGTH: 106
<212> TYPE: PRT
<213> ORGANISM: Artificial
<220> FEATURE:
<223> OTHER INFORMATION: synthetic construct

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Arg Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Leu Arg Pro Leu Thr
                85                  90                  95

Phe Gly Gly Gly Thr Lys Val Glu Ile Lys
            100                 105
```

<210> SEQ ID NO 11
<211> LENGTH: 124
<212> TYPE: PRT
<213> ORGANISM: Artificial
<220> FEATURE:
<223> OTHER INFORMATION: synthetic construct

<400> SEQUENCE: 11

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Arg Lys Val
            20                  25                  30

Gly Arg Ser Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
    50                  55                  60

Leu Arg Asn Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Ala Ile Thr Thr Val Ile Gly Gly Thr Phe Asp
            100                 105                 110

Tyr Trp Gly Gln Gly Thr Thr Val Thr Val Ser Ser
        115                 120

<210> SEQ ID NO 12
<211> LENGTH: 124
<212> TYPE: PRT
<213> ORGANISM: Artificial
<220> FEATURE:
<223> OTHER INFORMATION: synthetic construct

<400> SEQUENCE: 12

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Lys Val
            20                  25                  30

Gly Ser Ser Val Ser Trp Ile Arg Gln Pro Pro Gly Lys Gly Leu Glu
        35                  40                  45

Trp Ile Gly His Ile Tyr Trp Asp Asp Lys Arg Leu Asn Pro Ser
    50                  55                  60

Leu Arg Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Ala Ile Thr Thr Val Ile Gly Gly Thr Phe Asp
            100                 105                 110

Leu Trp Gly Gln Gly Thr Leu Val Thr Val Ser Ser
        115                 120

<210> SEQ ID NO 13
<211> LENGTH: 10
<212> TYPE: PRT
<213> ORGANISM: Artificial
<220> FEATURE:
<223> OTHER INFORMATION: synthetic construct

<400> SEQUENCE: 13

Ser Ala Ser Ser Ser Ile Ser Tyr Met His
1               5                   10

<210> SEQ ID NO 14
<211> LENGTH: 7
<212> TYPE: PRT
<213> ORGANISM: Artificial
<220> FEATURE:
<223> OTHER INFORMATION: synthetic construct

<400> SEQUENCE: 14
```

Asp Thr Ser Lys Leu Ala Arg
1               5

<210> SEQ ID NO 15
<211> LENGTH: 9
<212> TYPE: PRT
<213> ORGANISM: Artificial
<220> FEATURE:
<223> OTHER INFORMATION: synthetic construct

<400> SEQUENCE: 15

Gln Gln Trp Tyr Arg Asn Pro Leu Thr
1               5

<210> SEQ ID NO 16
<211> LENGTH: 9
<212> TYPE: PRT
<213> ORGANISM: Artificial
<220> FEATURE:
<223> OTHER INFORMATION: synthetic construct

<400> SEQUENCE: 16

Gln Gln Trp Tyr Arg His Pro Leu Thr
1               5

<210> SEQ ID NO 17
<211> LENGTH: 9
<212> TYPE: PRT
<213> ORGANISM: Artificial
<220> FEATURE:
<223> OTHER INFORMATION: synthetic construct

<400> SEQUENCE: 17

Gln Gln Trp Tyr Arg Ser Pro Leu Thr
1               5

<210> SEQ ID NO 18
<211> LENGTH: 9
<212> TYPE: PRT
<213> ORGANISM: Artificial
<220> FEATURE:
<223> OTHER INFORMATION: synthetic construct

<400> SEQUENCE: 18

Gln Gln Trp Tyr Arg Thr Pro Leu Thr
1               5

<210> SEQ ID NO 19
<211> LENGTH: 9
<212> TYPE: PRT
<213> ORGANISM: Artificial
<220> FEATURE:
<223> OTHER INFORMATION: synthetic construct

<400> SEQUENCE: 19

Gln Gln Trp Tyr Arg Ala Pro Leu Thr
1               5

<210> SEQ ID NO 20
<211> LENGTH: 9
<212> TYPE: PRT
<213> ORGANISM: Artificial
<220> FEATURE:
<223> OTHER INFORMATION: synthetic construct

<400> SEQUENCE: 20

Gln Gln Trp Tyr Leu Asn Pro Leu Thr

-continued

<210> SEQ ID NO 21
<211> LENGTH: 9
<212> TYPE: PRT
<213> ORGANISM: Artificial
<220> FEATURE:
<223> OTHER INFORMATION: synthetic construct

<400> SEQUENCE: 21

Gln Gln Trp Tyr Leu His Pro Leu Thr
1               5

<210> SEQ ID NO 22
<211> LENGTH: 9
<212> TYPE: PRT
<213> ORGANISM: Artificial
<220> FEATURE:
<223> OTHER INFORMATION: synthetic construct

<400> SEQUENCE: 22

Gln Gln Trp Tyr Leu Arg Pro Leu Thr
1               5

<210> SEQ ID NO 23
<211> LENGTH: 12
<212> TYPE: PRT
<213> ORGANISM: Artificial
<220> FEATURE:
<223> OTHER INFORMATION: synthetic construct

<400> SEQUENCE: 23

Gly Phe Ser Leu Arg Lys Val Gly Arg Ser Val Ser
1               5                   10

<210> SEQ ID NO 24
<211> LENGTH: 12
<212> TYPE: PRT
<213> ORGANISM: Artificial
<220> FEATURE:
<223> OTHER INFORMATION: synthetic construct

<400> SEQUENCE: 24

Gly Phe Ser Leu Arg Lys Val Gly Ser Ser Val Ser
1               5                   10

<210> SEQ ID NO 25
<211> LENGTH: 16
<212> TYPE: PRT
<213> ORGANISM: Artificial
<220> FEATURE:
<223> OTHER INFORMATION: synthetic construct

<400> SEQUENCE: 25

His Ile Tyr Trp Asp Asp Asp Lys Arg Tyr Asn Pro Ser Leu Arg Asn
1               5                   10                  15

<210> SEQ ID NO 26
<211> LENGTH: 16
<212> TYPE: PRT
<213> ORGANISM: Artificial
<220> FEATURE:
<223> OTHER INFORMATION: synthetic construct

<400> SEQUENCE: 26

His Ile Tyr Trp Asp Asp Asp Lys Arg Leu Asn Pro Ser Leu Arg Asn
1               5                   10                  15

```
<210> SEQ ID NO 27
<211> LENGTH: 14
<212> TYPE: PRT
<213> ORGANISM: Artificial
<220> FEATURE:
<223> OTHER INFORMATION: synthetic construct

<400> SEQUENCE: 27

Arg Ala Ile Thr Thr Val Ile Gly Gly Gly Thr Phe Asp Tyr
1               5                   10

<210> SEQ ID NO 28
<211> LENGTH: 14
<212> TYPE: PRT
<213> ORGANISM: Artificial
<220> FEATURE:
<223> OTHER INFORMATION: synthetic construct

<400> SEQUENCE: 28

Arg Ala Ile Thr Thr Val Ile Gly Gly Gly Thr Phe Asp Leu
1               5                   10

<210> SEQ ID NO 29
<211> LENGTH: 25
<212> TYPE: PRT
<213> ORGANISM: Homo sapiens

<400> SEQUENCE: 29

Ala Asn Tyr Cys Ser Gly Glu Cys Glu Phe Val Phe Leu Gln Lys Tyr
1               5                   10                  15

Pro His Thr His Leu Val His Gln Ala
            20                  25

<210> SEQ ID NO 30
<211> LENGTH: 15
<212> TYPE: PRT
<213> ORGANISM: Homo sapiens

<400> SEQUENCE: 30

Cys Ser Gly Glu Cys Glu Phe Val Phe Leu Gln Lys Tyr Pro His
1               5                   10                  15

<210> SEQ ID NO 31
<211> LENGTH: 15
<212> TYPE: PRT
<213> ORGANISM: Homo sapiens

<400> SEQUENCE: 31

Gly Glu Cys Glu Phe Val Phe Leu Gln Lys Tyr Pro His Thr His
1               5                   10                  15

<210> SEQ ID NO 32
<211> LENGTH: 213
<212> TYPE: PRT
<213> ORGANISM: Artificial
<220> FEATURE:
<223> OTHER INFORMATION: synthetic construct

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45
```

```
Asp Thr Ser Lys Leu Ala Arg Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Tyr Leu His Pro Leu Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 33
<211> LENGTH: 450
<212> TYPE: PRT
<213> ORGANISM: Artificial
<220> FEATURE:
<223> OTHER INFORMATION: synthetic construct

<400> SEQUENCE: 33

Gln Leu Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Arg Lys Val
             20                  25                  30

Gly Ser Ser Val Ser Trp Ile Arg Gln Pro Pro Gly Lys Gly Leu Glu
         35                  40                  45

Trp Ile Gly His Ile Tyr Trp Asp Asp Asp Lys Arg Leu Asn Pro Ser
     50                  55                  60

Leu Arg Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Arg Ala Ile Thr Thr Val Ile Gly Gly Thr Phe Asp
            100                 105                 110

Leu Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

Val Thr Val Pro Ser Ser Leu Gly Thr Lys Thr Tyr Thr Cys Asn
        195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser Gln
        260                 265                 270

Glu Asp Pro Glu Val Gln Phe Asn Trp Tyr Val Asp Gly Val Glu Val
    275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Gln Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
            405                 410                 415

Asp Lys Ser Arg Trp Gln Glu Gly Asn Val Phe Ser Cys Ser Val Met
        420                 425                 430

His Glu Ala Leu His Asn His Tyr Thr Gln Lys Ser Leu Ser Leu Ser
    435                 440                 445

Leu Gly
    450

<210> SEQ ID NO 34
<211> LENGTH: 6
<212> TYPE: PRT
<213> ORGANISM: Artificial
<220> FEATURE:
<223> OTHER INFORMATION: Synthetic Construct

<400> SEQUENCE: 34

Asp Ile Gln Met Thr Gln
1               5

<210> SEQ ID NO 35
<211> LENGTH: 6
<212> TYPE: PRT
<213> ORGANISM: Artificial
<220> FEATURE:
<223> OTHER INFORMATION: SYNTHETIC CONSTRUCT

<400> SEQUENCE: 35

Pro Leu Thr Phe Gly Gly
1               5

<210> SEQ ID NO 36
<211> LENGTH: 195

```
-continued
<212> TYPE: DNA
<213> ORGANISM: Artificial
<220> FEATURE:
<223> OTHER INFORMATION: SYNTHETIC CONSTRUCT

<400> SEQUENCE: 36
tcgagagcca gacaaaaagc cagacattta gccagacact cgagagccag acaaaaagcc     60
agacatttag ccagacactc gagagccaga caaaaagcca gacatttagc cagacactcg    120
agagccagac aaaaagccag acatttagcc agacactcga gagccagaca aaaagccaga    180
catttagcca gacac                                                    195
```

US 8,063,188 B2

ANTI-MYOSTATIN ANTIBODIES

This application claims the benefit of U.S. Provisional Application Ser. No. 60/824,498 filed Sep. 5, 2006 and PCT Application Serial No. PCT/US2007/076604 filed Aug. 23, 2007, both of which are expressly incorporated herein by reference in their entirety.

FIELD OF THE INVENTION

The invention is in the field of medicine, particularly in the field of monoclonal antibodies against myostatin. More specifically the invention relates to anti-myostatin monoclonal antibodies that preferentially bind myostatin over GDF-11 and are resistant to protein cleavage, and use of the antibodies for treatment, prophylaxis or diagnosis of various disorders or conditions in mammalian and avian species.

BACKGROUND OF THE INVENTION

Myostatin, also referred to as growth differentiation factor-8 (GDF-8), is a member of the TGF-β superfamily of proteins, which shares structural similarities with other TGF-β family members. Myostatin is expressed largely in developing and adult skeletal muscle and functions as a negative regulator of skeletal muscle. Myostatin may also be involved in other physiological processes including preadipocyte differentiation to adipocytes, and, indirectly, with glucose homeostasis and inhibition of bone formation.

Growth differentiation factor-11, also referred to as GDF-11 or BMP-11, is the member of the TGF-β superfamily of proteins that is most homologous to myostatin. The amino acid sequence of the mature forms of human myostatin and GDF-11 are about 90% identical; however, GDF-11 is expressed in a wider range of tissues than is myostatin, including dental pulp, brain, heart, kidney and lung as well as muscle and adipose tissue. Human GDF-11 has recently been found to govern the temporal windows during which multipotent progenitors retain competence to produce distinct neural progeny.

There is a therapeutic need to specifically inhibit a myostatin activity while minimally inhibiting an activity of other TGF-β superfamily proteins, particularly GDF-11. Furthermore, there is a diagnostic need for an anti-myostatin antibody that minimally cross-reacts with another TGF-β superfamily protein, particularly GDF-11, in order to more accurately monitor or determine myostatin levels in a sample. Anti-myostatin antibodies that preferentially bind myostatin over GDF-11 are disclosed in International Publication Number WO 2005/094446. Humanized monoclonal antibodies which preferentially bind myostatin over GDF-11 are disclosed in International Publication Number WO 2007/044411.

Therapeutic antibodies may be subject to a variety of degradation reactions, e.g., deamidation or cleavage, that may occur in vivo or during manufacturing, formulation, storage and therapeutic use. For example, Asparagine (Asn) residues in antibodies or other polypeptides are particularly susceptible to cleavage in aqueous solution. Thus, there is a need for an anti-myostatin antibody that preferentially binds myostatin over GDF-11, has a strong binding affinity for myostatin (i.e., no greater than about $3\times10^{-8}$ M) and is resistant to chemical degradation.

SUMMARY OF THE INVENTION

Antibodies of the invention preferentially bind myostatin over GDF-11, i.e., they are significantly less reactive with GDF-11 than with myostatin. An antibody of the invention binds myostatin at least about 2, 3, 5, 10, 20, 22, or 25-times greater than it binds GDF-11 as measured by a technique in the art, e.g., by competition ELISA, or by BIACORE or KINEXA assay to demonstrate higher affinity (i.e., lower $K_D$) of the antibody to GDF-8 than GDF-11. Most preferably, antibodies of the invention do not bind GDF-11 above background levels in the binding assay used.

The present invention encompasses an anti-myostatin monoclonal antibody that preferentially binds myostatin over growth differentiation factor-11 (GDF-11), wherein said antibody binds myostatin with an affinity no greater than about $3\times10^{-8}$ M and wherein at least 95% of the monoclonal antibody is not cleaved when present for one year at 4° C., six months at 25° C., two months at 37° C. or four weeks at 40° C. in an antibody solution. An exemplary antibody solution comprises 1 mg/mL of an antibody of the invention, 10 mM phosphate, pH 7.4, and 150 mM NaCl. Preferably, antibodies of the invention are further characterized by having an $IC_{50}$ of less than 25 nM, in the in vitro myostatin/SBE reporter assay described in Example 4 herein.

In one embodiment, an antibody of the invention is resistant to chemical degradation, i.e., 100%, 99%, 98%, 97%, 96%, or 95% of the antibodies are not cleaved, when present in an antibody solution for a time and temperature selected from the group consisting of: one year at 4° C., six months at 25° C., two months at 37° C., and four weeks at 40° C. in an antibody solution. A preferred time and temperature is four weeks at 40° C.

In one embodiment, antibodies of the invention are further characterized by binding myostatin within the domain spanning amino acids 40-64 [ANYCSGECEFVFLQKYPHTH-LVHQA (SEQ ID NO: 29) for human], 43-57 [CSGECEFV-FLQKYPH (SEQ ID NO: 30) for human] or 45-59 [GECEFVFLQKYPHTH (SEQ ID NO: 31) for human] of mature myostatin. In another embodiment, antibodies of the invention are further characterized by binding a polypeptide consisting of amino acids 40-64, 43-57 or 45-59 of mature myostatin.

In one embodiment, an antibody of the invention comprises a heavy chain variable region (HCVR) with a sequence as shown in SEQ ID NO: 11 and a light chain variable region (LCVR) with a sequence selected from the group consisting of SEQ ID NO: 4, 5, 6, and 7. In another embodiment, a monoclonal antibody of the invention comprises a HCVR with a sequence as shown in SEQ ID NO: 12 and a LCVR with a sequence selected from the group consisting of SEQ ID NO: 9 and 10.

In one embodiment, an antibody of the invention comprises a HCVR and a LCVR, wherein said HCVR comprises a peptide at CDRH1 with the sequence as shown in SEQ ID NO: 23, a peptide at CDRH2 with the sequence as shown in SEQ ID NO: 25, and a peptide at CDRH3 with the sequence as shown in SEQ ID NO: 27, and wherein said LCVR comprises a peptide at CDRL1 with the sequence as shown in SEQ ID NO: 13, a peptide at CDRL2 with the sequence as shown in SEQ ID NO: 14, and a peptide at CDRL3 with the sequence selected from the group consisting of SEQ ID NO: 16, 17, 18 and 19.

In another embodiment, an antibody of the invention comprises a HCVR and a LCVR, wherein said HCVR comprises a peptide at CDRH1 with the sequence as shown in SEQ ID NO: 24, a peptide at CDRH2 with the sequence as shown in SEQ ID NO: 26, and a peptide at CDRH3 with the sequence as shown in SEQ ID NO: 28, and wherein said LCVR comprises a peptide at CDRL1 with the sequence as shown in SEQ ID NO: 13, a peptide at CDRL2 with the sequence as shown in SEQ ID NO: 14, and a peptide at CDRL3 with the sequence selected from the group consisting of SEQ ID NO: 21, and 22.

In one embodiment, an antibody of the invention further comprises a constant region, wherein said constant region originates from the human genome or the genome of an animal selected from the group consisting of domestic animals, sports animals and food-source animals. In a more preferred embodiment, an antibody of the invention comprises a light chain with an amino acid sequence as shown in SEQ ID NO: 32 and a heavy chain with an amino acid sequence as shown in SEQ ID NO: 33.

In another embodiment, the invention provides a composition (e.g., a pharmaceutical composition) comprising an antibody of the invention. The composition of the invention may further comprise a pharmaceutically acceptable carrier. In said composition, the antibody of the invention is the active ingredient. Preferably the composition comprises a homogeneous or substantially homogeneous population of an anti-myostatin antibody of the invention. The composition for therapeutic or prophylactic use is sterile, may be lyophilized, and is preferably supplied with an appropriate diluent.

The invention provides a method of inhibiting at least one myostatin biological activity in an animal, preferably a mammalian or avian species, preferably a human, in need thereof, comprising administering a therapeutically effective amount or prophylactically effective amount of an anti-myostatin monoclonal antibody of the invention to said mammalian or avian species. The invention further provides a method of enhancing muscle mass or treating or preventing a disease or disorder or condition ameliorated by neutralizing or antagonizing a myostatin bioactivity that comprises administering to a patient (e.g., a human) in need of such treatment or prevention a therapeutically or prophylactically effective amount of an antibody of the invention.

The invention embodies an antibody of the invention for use in therapy.

The invention embodies the use of an antibody of the invention for the preparation of a medicament for the treatment of muscle wasting, frailty, age-related sarcopenia, disuse atrophy and cachexia.

The invention embodies the use of an antibody of the invention for the preparation of a medicament for the prevention of muscle wasting, frailty, age-related sarcopenia, disuse atrophy and cachexia.

The invention embodies the method of treating muscle wasting, frailty, age-related sarcopenia, disuse atrophy and cachexia in a mammal, preferably a human, in need thereof by administering a therapeutically effective amount of an antibody of the invention.

The invention embodies the method of preventing muscle wasting, frailty, age-related sarcopenia, disuse atrophy and cachexia in a mammal, preferably a human, in need thereof by administering a prophylactically effective amount of an antibody of the invention.

BRIEF DESCRIPTION OF THE DRAWINGS

FIG. 1A shows the alignment of the amino acid sequence of the mature form of human myostatin and human GDF-11 with the antigenic epitope of Mabs 510C2 and C12 and their variants underlined and the residues within the antigenic epitope that differ between myostatin and GDF-11 in bold print.

FIG. 1B lists antigenic epitopes that Mabs 510C2 and C12 and their variants bind.

FIGS. 2A and B show the amino acid sequences of the variable regions of the parent Mabs 510C2 and C12 respectively, as well as several variants, including CDR domains and frameworks. The CDR domains are in bold print and the variations in the CDR domains are underlined.

FIG. 3 shows the alignment of the amino acid sequence of the CDR domains of parent Mabs 510C2 and C12 and antibodies of the present invention. The variations are in bold print and underlined.

FIG. 4 lists the amino acid sequences of the light chain and heavy chain of a monoclonal antibody of the invention, i.e., N93H-C12.

FIGS. 5A and B compare binding affinity of certain monoclonal antibodies of the invention with that of their parent antibody as determined by ELISA.

DETAILED DESCRIPTION OF THE INVENTION

Definitions

When used herein, the term "mature myostatin" (see SEQ ID NO: 1 for human, murine, rat, chicken, turkey, canine, equine and porcine species) refers to the monomeric or the homodimeric form of the protein resulting after proteolytic cleavage, e.g., for humans at Arg 266 of the 375 amino acid proprotein form of myostatin. When used herein, the term "myostatin" refers to mature myostatin unless otherwise stated herein.

A full-length antibody as it exists naturally is an immunoglobulin molecule comprised of four peptide chains, two heavy (H) chains (about 50-70 kDa when full length) and two light (L) chains (about 25 kDa when full length) interconnected by disulfide bonds. The amino terminal portion of each chain includes a variable region of about 100-110 or more amino acids primarily responsible for antigen recognition. The carboxy-terminal portion of each chain defines a constant region primarily responsible for effector function.

Light chains are classified as kappa or lambda and characterized by a particular constant region as known in the art. Each heavy chain type is characterized by a particular constant region known in the art. $IgG_1$ and $IgG_4$ are preferred isotypes for antibodies of the invention. Each heavy chain is comprised of an N-terminal heavy chain variable region (herein "HCVR") and a heavy chain constant region. The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region (herein "LCVR") and a light chain constant region, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, and FR4. Herein the 3 CDRs of the heavy chain are referred to as "CDRH1, CDRH2, and CDRH3" and the 3 CDRs of the light chain are referred to as "CDRL1, CDRL2 and CDRL3." The CDRs contain most of the residues which form specific interactions with the antigen. Assignment of amino acids to each domain is in accordance with well-known conventions [Kabat, "Sequences of Proteins of Immunological Interest," National Institutes of Health, Bethesda, Md. (1991)]. The functional ability of an antibody to bind a particular antigen is largely influenced by the six CDRs.

The term "antibody," in reference to an anti-myostatin monoclonal antibody of the invention (or simply, "monoclonal antibody of the invention" or "antibody of the invention"), as used herein, refers to a monoclonal antibody. A "monoclonal antibody" or "Mab" as used herein refers to a chimeric antibody, a humanized antibody or a fully human antibody, unless otherwise indicated herein. Preferably a monoclonal antibody of the invention exists in a homogeneous or substantially homogeneous population. Monoclonal antibodies of the invention can be produced using hybridoma techniques well known in the art, as well as recombinant technologies, phage display technologies, synthetic technologies or combinations of such technologies or other technologies readily known in the art. "Monoclonal antibody" refers to an antibody that is derived from a single copy or clone, including e.g., any eukaryotic, prokaryotic, or phage clone, and not the method by which it is produced. A "monoclonal antibody" can be an intact antibody (comprising a complete or full length Fc region), a substantially intact antibody, or a portion or fragment of an antibody comprising an antigen-binding portion, e.g., a Fab fragment, Fab' fragment or F(ab')$_2$ fragment of a chimeric, humanized or human antibody.

The variable regions of each light/heavy chain pair form the antigen-binding sites of the antibody. Thus, an intact IgG antibody has two binding sites. Except in bifunctional or bispecific antibodies, the two binding sites are the same. As used herein, the "antigen-binding portion" or "antigen-binding region" or "antigen-binding fragment" refers interchangeably to that portion of an antibody molecule, within the variable region, which contains the amino acid residues that interact with an antigen and confer on the antibody its specificity and affinity for the antigen. The antigen-binding portion of the antibody includes framework amino acid residues necessary to maintain the proper conformation of the antigen-binding residues. Preferably, the framework regions of antibodies of the invention are of human origin or substantially of human origin (at least 85%, 90%, 95%, 97% or 99% of human origin).

Furthermore, a "monoclonal antibody" as used herein can be a single chain Fv fragment that may be produced by joining the DNA encoding the LCVR and HCVR with a linker sequence. (See, Pluckthun, *The Pharmacology of Monoclonal Antibodies*, vol. 113, Rosenburg and Moore eds., Springer-Verlag, New York, pp 269-315, 1994). It is understood that regardless of whether fragments or portions are specified, the term "antibody" as used herein includes such fragments or portions as well as single chain forms. As long as the protein retains the ability to specifically or preferentially bind its intended target (i.e., epitope or antigen), it is included within the term "antibody."

A "parent" antibody, as used herein, is one which is encoded by an amino acid sequence used for the preparation of the modified antibody or variant. The parent antibody may have a murine framework, but preferably has a human framework region. The parent antibody may be a murine, chimeric, humanized or human antibody.

A "modified" or "variant" anti-myostatin antibody refers herein to a molecule which differs in amino acid sequence from a "parent" anti-myostatin antibody amino acid sequence by virtue of addition, deletion and/or substitution of one or more amino acid residue(s) in the parent antibody sequence. In a preferred embodiment, the variant antibody comprises one or more amino acid substitution(s) in the variable region compared to the parent antibody. An antibody of the invention (a variant antibody) retains the ability of its parent antibody to preferentially bind myostatin over GDF-11, has myostatin binding affinity similar to or better than that of its parent antibody and has stability properties (i.e., chemical stability properties) which are superior to those of the parent antibody.

"Chemical stability" refers to the ability to withstand chemical degradation, e.g., cleavage at a peptide bond ("cleavage"). Antibodies of the invention that are "resistant to chemical degradation" as used herein are resistant to spontaneous cleavage at a peptide bond and have increased chemical stability as compared to the parent antibody. Preferably, 100%, 99%, 98%, 97%, 96%, or 95% of an antibody of the invention is resistant to chemical degradation, i.e., is not cleaved, when present for one year at 4° C., six months at 25° C., two months at 37° C., or four weeks at 40° C. in an antibody solution. An antibody solution is a solution used in an antibody pharmaceutical composition. A preferred antibody solution comprises 1 mg/mL of the antibody, 10 mM phosphate, pH 7.4 and 150 mM NaCl.

A modified anti-myostatin antibody of particular interest herein is an anti-myostatin monoclonal antibody with increased chemical stability over that of the parent antibody, in which a labile Asn residue of an Asn-Pro dipeptide within the parent antibody is eliminated, preferably by substitution with a natural amino acid residue, even more preferably by substitution with a histidine (H), serine (S), threonine (T), alanine (A), or arginine (R) residue. Further, such modified antibody is characterized by preferentially binding myostatin over GDF-11 and having a $K_D$ for myostatin of less than about $3 \times 10^{-8}$ M, preferably further characterized by having an $IC_{50}$ of less than 25 nM in an in vitro myostatin/SBE reporter assay as set forth in Example 4 herein.

The term "labile Asn residue," as used herein, refers to an asparagine residue in an antibody, protein, or polypeptide, at which spontaneous deamidation or peptide bond cleavage may occur in vitro or in vivo.

The term "cleaved or cleavage," as used herein, refers to cleavage of a peptide bond in an antibody. A cleavage site of particular interest is at an Asn residue in an antibody, either at the amino or carboxy end of the Asn residue. Cleavage of an antibody may lead to a reduction of stability and/or the reduction or loss of activity of a protein, or loss of binding affinity of an antibody. The spontaneous modification leading to cleavage may occur ex vivo during the preparation of the formulated therapeutic, negatively impacting the manufacturing and storage of the pharmaceutical agent. Cleavage may also occur ex vivo during the manufacturing or storage of the antibody. Moreover, the spontaneous modification may occur in vivo affecting the efficacy of the protein or antibody and duration of action. However, simply substituting an amino acid at a cleavage site for any other amino acid may negatively impact a desirable bioactivity of an antibody, for example, binding affinity or neutralization.

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics.

The term "epitope," as used herein, further refers to a portion of a polypeptide having antigenic and/or immunogenic activity in an animal, preferably a mammal, e.g., a mouse or a human. The term "antigenic epitope," as used herein, is defined as a portion of a polypeptide to which an antibody can specifically bind as determined by any method well known in the art, for example, by conventional immunoassays. Antigenic epitopes need not necessarily be immunogenic, but may be immunogenic. An "immunogenic epitope," as used herein, is defined as a portion of a polypeptide that elicits an antibody response in an animal, as determined by any method known in the art. (See, e.g., Geysen et al., *Proc. Natl. Acad. Sci. USA* 81:3998-4002 (1983)).

The phrases "biological property" or "bioactivity," "activity" or "biological activity," in reference to an antibody of the present invention, are used interchangeably herein and include, but are not limited to, epitope/antigen affinity and specificity, ability to neutralize or antagonize an activity of myostatin in vivo or in vitro, $IC_{50}$ in a myostatin/SBE reporter assay as shown in Example 4 herein, or other in vitro activity assay, the in vitro or in vivo stability of the antibody. Other identifiable biological properties of an antibody include, for example, cross-reactivity, (i.e., with non-human homologs of the targeted peptide, or with other proteins or tissues, generally), and ability to preserve high expression levels of protein in mammalian cells. The aforementioned properties or characteristics can be observed or measured or assessed using art-recognized techniques including, but not limited to, ELISA, competitive ELISA, surface plasma resonance analysis, in vitro and in vivo neutralization assays without limit, receptor binding, BIACORE or KINEXA assays, cytokine or growth factor production and/or secretion, Xenopus animal cap development, signal transduction and immunohistochemistry with tissue sections from different sources including human, primate, or any other source as the need may be.

The term "myostatin activity" as used herein refers to one or more of physiologically growth-regulatory or morphogenetic activities associated with active myostatin protein. For example, active myostatin is a negative regulator of skeletal muscle mass. Active myostatin can also modulate the production of muscle-specific enzymes (e.g., creatine kinase), stimulate myoblast proliferation, and modulate preadipocyte differentiation to adipocytes.

The term "inhibit" or "neutralize" as used herein with respect to an activity of an antibody of the invention means the ability to substantially antagonize, prohibit, prevent, restrain, slow, disrupt, eliminate, stop, reduce or reverse e.g., progression or severity of that which is being inhibited including, but not limited to, a biological activity. The inhibition or neutralization is preferably at least about 10%, 20%, 30%, 40%, 50%, 60%, 70%, 80%, 90%, 95% or higher of the activity in the absence of the antibody.

The terms "individual," "subject," and "patient," used interchangeably herein, refer to an animal, preferably a mammalian (including a nonprimate and a primate) or avian species, including, but not limited to, murines, simians, humans, mammalian farm animals (e.g., bovine, porcine, ovine), mammalian sport animals (e.g., equine), and mammalian pets (e.g., canine and feline); preferably the term refers to humans. The term also refers to avian species, including, but not limited to, chickens and turkeys. In a certain embodiment, the subject, preferably a mammal, more preferably a human, is further characterized with a disease or disorder or condition that would benefit from a decreased level or decreased bioactivity of myostatin. In another embodiment the subject, preferably a mammal, preferably a human, is further characterized as being at risk of developing a disorder, disease or condition that would benefit from a decreased level of myostatin or a decreased bioactivity of myostatin.

Antibody Characterization

The invention presents an antibody that preferentially binds myostatin over GDF 11 and is more stable than the parent antibody (i.e., more resistant to chemical degradation than the parent antibody) while maintaining, or improving, the binding affinity for myostatin as exhibited by the parent antibody. In one embodiment, a labile Asn residue in CDRL3 of the parent antibody, Mab C12 or Mab 510C2 as shown in FIG. 2, is substituted with a different amino acid.

Preferred amino acid substitutions in an antibody of the invention are those which: (1) reduce susceptibility to spontaneous chemical degradation, i.e., cleavage or deamidation, and (2) maintain the antigen-antibody binding affinity as exhibited by the parent antibody. In one preferred embodiment, the Asn residue in the CDRL3 of Mab C12 is replaced with H or R. In another preferred embodiment, the Asn residue in the CDRL3 of Mab 510C2 is replaced with H, S, T, or A.

In one embodiment, an antibody of the invention is resistant to spontaneous chemical degradation, i.e., 100%, 99%, 98%, 97%, 96%, or 95% of the antibodies are not cleaved when present in an antibody solution for a time and temperature selected from the group consisting of: one year at 4° C., six months at 25° C., two months at 37° C., and four weeks at 40° C. in an antibody solution. An antibody solution is any solution suitable for a pharmaceutical composition comprising an antibody. An exemplary antibody solution comprises 1 mg/mL of the antibody, 10 mM phosphate, pH 7.4 and 150 mM NaCl.

In one embodiment, antibodies of the invention are further characterized by having a strong binding affinity ($K_D$) for myostatin, i.e., less than about $3 \times 10^{-8}$ M, $1 \times 10^{-8}$ M or $1 \times 10^{-9}$ M, preferably less than about $9 \times 10^{-10}$ M, $8.7 \times 10^{-10}$ M or more preferably, less than about $8 \times 10^{-11}$ M. Alternatively, the antibodies of the invention are characterized by a $K_D$ for myostatin of no greater than about $3 \times 10^{-8}$ M, $1 \times 10^{-8}$ M, $1 \times 10^{-9}$ M or $9 \times 10^{-10}$ M, more preferably no greater than about $8.7 \times 10^{-10}$ M and most preferably no greater than about $8 \times 10^{-11}$ M. The binding affinity of an antibody of the invention is similar to or better than that of its parent antibody.

Preferably, antibodies of the invention characterized by a strong binding affinity as described above also have an $IC_{50}$ of less than 25 nM, 20 nM, 16 nM, 14 nM, 10 nM, 9 nM, 6 nM, or 5.2 nM in the in vitro myostatin/SBE reporter assay as set forth in Example 4 herein. Preferably the $IC_{50}$ of an antibody of the invention is similar to or better than that of its parent antibody. All antibodies of the invention are significantly less reactive with GDF-11 than with myostatin, i.e., they preferentially bind myostatin over GDF-11.

Antibodies of the invention are preferably chimeric, humanized or human antibodies or antigen-binding portions thereof and preferably bind to myostatin within the region of the mature form of myostatin spanning amino acids 40-64 or more preferably within the region of the mature form of myostatin spanning amino acids 43-57 and/or 45-59. Furthermore, antibodies of the invention neutralize a myostatin biological activity in vivo or in vitro. Specific binding of anti-myostatin monoclonal antibodies of the invention allows the antibodies of the invention to be used as therapeutics or prophylactics for myostatin-associated conditions, diseases or disorders, i.e., conditions, diseases or disorders which benefit from lowering myostatin levels or antagonizing or inhibiting a myostatin biological activity. Further, antibodies of the invention may be used to diagnose or monitor conditions, diseases or disorders which benefit from an altered level or bioactivity of myostatin or to determine the level of myostatin in a sample.

The anti-myostatin monoclonal antibodies of the invention bind an antigenic epitope discovered to be localized within amino acids 40-64 (SEQ ID NO: 1 for human) of mature myostatin preferably within amino acids 43-57 and/or 45-59 of mature myostatin. Furthermore, a myostatin immunogenic epitope of the invention is localized within amino acids 40-64 of mature myostatin (SEQ ID NO: 1 for human), preferably within amino acids 43-57 and/or 45-59 of mature myostatin of any mammalian or avian species. An immunogenic epitope of the invention is also contemplated to be an antigenic epitope. Additionally, residues of myostatin outside of the amino acids 40-64 may affect the conformational structure of the antigenic domain and thereby alter binding of an antibody of the invention to the antigenic epitope.

Single chain antibodies, and chimeric, humanized antibodies, as well as chimeric or CDR-grafted single chain antibodies, and the like, comprising portions derived from different species, are also encompassed by the present invention and the term "antibody" or "modified antibody." The various portions of these antibodies can be joined together chemically by conventional techniques, synthetically, or can be prepared as a contiguous protein using genetic engineering techniques. For example, nucleic acids encoding a chimeric or humanized chain can be expressed to produce a contiguous protein.

In addition, functional portions of antibodies, including antigen-binding portions of chimeric, humanized, human or single chain antibodies, can also be produced. Functional portions of the foregoing antibodies retain at least one antigen-binding function and/or biological function or bioactivity of the full-length antibody from which they are derived. Preferred functional portions retain an antigen-binding function of a corresponding full-length antibody (e.g., the ability to bind a mammalian mature form of myostatin). Particularly preferred functional portions or fragments retain the ability to inhibit one or more functions or bioactivities characteristic of a mammalian mature myostatin, such as a binding activity, a signaling activity, and/or stimulation of a cellular response. For example, in one embodiment, a functional portion or fragment can inhibit the interaction of mature myostatin with one or more of its ligands and/or can inhibit one or more receptor-mediated functions.

Antibody portions or fragments capable of binding to mature myostatin or a portion thereof (preferably within amino acids 40-64, 43-57 and/or 45-59 of mature myostatin), include, but are not limited to, Fv, Fab, Fab' and F(ab')$_2$ fragments and are encompassed by the invention. Such fragments can be produced by enzymatic cleavage or by recombinant techniques. For instance, papain or pepsin cleavage can generate Fab or F(ab')$_2$ fragments, respectively. The smallest antigen-binding fragment is the Fv, which consists of the HCVR and the LCVR domains. The Fab fragment consists of the HCVR-CH1 and LCVR-CL domains covalently linked by a disulfide bond between the constant regions. To overcome the tendency of non-covalently linked HCVR and LCVR domains in the Fv to dissociate when co-expressed in a host cell, a so-called single chain (sc) Fv fragment (scFv) can be constructed, in which a flexible and adequately long polypeptide links either the C-terminus of the HCVR to the N-terminus of the LCVR or the C-terminus of the LCVR to the N-terminus of the HCVR. A commonly used linker is a 15-residue (Gly$_4$Ser)$_3$ peptide, but other linkers are also known in the art. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Identification of Labile Asn Residue(s)

Many methods are available to detect and quantify the spontaneous modifications of labile Asn residues in a protein, e.g., antibody. Deamidation, a modification resulting in the conversion of an asparagine residue to a mixture of isoaspartate and aspartate which may provide a signal for protein degradation, introduces negative charge and changes the protein mass (NH$_2$ vs OH, Δ=1 Da) and hydrophobicity. Separation techniques including electronic and chromatographic methods, such as, IEF, cIEF, urea gel electrophoresis, reversed-phase PHLC, ion exchange PHLC, and hydrophilic interaction, may be used to separate or isolate deamidated or cleaved forms of an antibody, or a protein or a polypeptide. Ion-exchange chromatography is widely used to isolate deamidated proteins. The location and extent of the spontaneous modifications of an antibody, or a protein, or a polypeptide may be further characterized by liquid-chromatography/mass spectrometry (LC/MS) and N-terminal sequencing.

Substitution of Labile Asn Residue(s) or Other Modification of Antibodies

To eliminate, e.g., by amino acid substitution, a labile Asn residue in an antibody, or other protein, the labile Asn residue may be substituted with a single amino acid. It is desirable that the amino acid substitution does not alter (i.e., negatively), or minimally alters (e.g., 10%, 5%, 4%, 3%, 2% or less) the antibody:antigen binding affinity. It is further desirable that the amino acid substitution does not alter (i.e., negatively), or minimally alters antibody neutralization, epitope specificity and the ability of the antibody to preferentially bind myostatin over GDF-11. An ELISA may be used to determine the effects of the individual amino acid substitutions on the binding affinity of an antibody of the invention to myostatin or an antigenic epitope thereof and the ELISA value compared to that of its parent antibody (e.g., C12 or 510C2 antibody) binding to the same antigen. Alternatively, a BIACORE® or KINEXA® assay may be used to measure binding affinity of an antibody.

Antibodies of the invention may be further mutagenized (or mutagenized prior to elimination of the Asn residue whose presence contributes to the parent antibody instability), e.g., within the CDR domain(s) to create a variant antibody with an optimized property of interest, e.g., binding affinity, IC$_{50}$, specificity, etc. An antibody of the invention generated by amino acid substitution is preferred and has at least one amino acid residue of the parent antibody molecule removed and a different residue inserted in its place. The sites of greatest interest for such substitutional mutagenesis include the CDR regions, but FR alterations are also contemplated.

A convenient way for generating substitutional variants is affinity maturation using phage display. Briefly, several CDR region sites are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity, specificity, IC$_{50}$) as herein disclosed. In order to identify candidate CDR region sites for modification, alanine scanning mutagens can be performed to identify CDR region residues contributing significantly to antigen binding. Alternatively, or in addition, it may be beneficial to analyze a crystal structure of the antigen-antibody complex to identify contact points between the antibody and myostatin. Such contact residues and neighboring residues are candidates for substitution according to the techniques elaborated herein or known in the art. Alternatively, or in addition, random mutagenesis may be performed on one or more CDR sequences at one or more residue positions, either while the CDR is operably linked to the variable region or while the CDR is independent of other variable region sequence and then the altered CDR returned to a variable region using recombinant DNA technology. Once such variant antibodies are generated and expressed, the panel of variants is subjected to screening as described herein and antibodies with superior properties in one or more relevant assays may be selected for further development.

Antibody Expression

The present invention is also directed to cell lines that express an anti-myostatin monoclonal antibody of the invention or portion thereof. Creation and isolation of cell lines producing a monoclonal antibody of the invention can be accomplished using standard techniques known in the art. Preferred cell lines include COS, CHO, SP2/0, NS0 and yeast (available from public repositories such as ATCC, American Type Culture Collection, Manassas, Va.).

A wide variety of host expression systems can be used to express an antibody of the present invention including prokaryotic (bacterial) and eukaryotic expression systems (such as yeast, baculovirus, plant, mammalian and other animal cells, transgenic animals, and hybridoma cells), as well as phage display expression systems. An example of a suitable bacterial expression vector is pUC119 and a suitable eukaryotic expression vector is a modified pcDNA3.1 vector with a weakened DHFR selection system. Other antibody expression systems are also known in the art and are contemplated herein.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably linked in one vector or, alternatively, the heavy chain and the light chain may be expressed independently from different promoters to which they are operably linked in two vectors—one expressing the heavy chain and one expressing the light chain. Optionally the heavy chain and light chain may be expressed in different host cells. Preferably, the recombinant antibodies are secreted into the medium in which the host cells are cultured, from which the antibodies can be recovered or purified. Standard recombinant DNA methodologies are used to obtain antibody heavy and light chain genes, incorporate these genes into recombinant expression vectors, and introduce the vectors into host cells.

An isolated DNA encoding a HCVR region can be converted to a full-length heavy chain gene by operably linking the HCVR-encoding DNA to another DNA molecule encoding heavy chain constant regions (CH1, CH2, and CH3). The sequences of human heavy chain constant region genes are known in the art. See, e.g., Kabat, et al., *Sequences of Proteins of Immunological Interest*, Fifth Edition, U.S. Department of Health and Human Services, NIH Publication No. 91-3242 (1991). DNA fragments encompassing these regions can be obtained e.g., by standard PCR amplification. The heavy chain constant region can be of any type, (e.g., IgG, IgA, IgE, IgM or IgD), class (e.g., $IgG_1$, $IgG_2$, $IgG_3$ and $IgG_4$) or subclass constant region and any allotypic variant thereof as described in Kabat (supra). Alternatively, the antigen binding portion can be a Fab fragment, Fab' fragment, $F(ab')_2$ fragment, Fd, or a single chain Fv fragment (scFv). For a Fab fragment heavy chain gene, the HCVR-encoding DNA may be operably linked to another DNA molecule encoding only a heavy chain CH1 constant region.

An isolated DNA encoding a LCVR region may be converted to a full-length light chain gene (as well as to a Fab light chain gene) by operably linking the LCVR-encoding DNA to another DNA molecule encoding a light chain constant region, CL. The sequences of human light chain constant region genes are known in the art. See, e.g., Kabat, supra. DNA fragments encompassing these regions can be obtained by standard PCR amplification. The light chain constant region can be a kappa or lambda constant region.

To create an scFv gene, the HCVR- and LCVR-encoding DNA fragments are operably linked to another fragment encoding a flexible linker, e.g., encoding the amino acid sequence $(Gly_4\text{-}Ser)_3$, such that the HCVR and LCVR sequences can be expressed as a contiguous single-chain protein, with the LCVR and HCVR regions joined by the flexible linker.

To express an antibody of the invention, a DNA encoding a partial or full-length light and/or heavy chain, obtained as described above, is inserted into an expression vector such that the gene is operably linked to transcriptional and translational control sequences. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods. Additionally, the recombinant expression vector can encode a signal peptide that facilitates secretion of the anti-myostatin monoclonal antibody light and/or heavy chain from a host cell. The anti-myostatin monoclonal antibody light and/or heavy chain gene can be cloned into the vector such that the signal peptide is operably linked in-frame to the amino terminus of the antibody chain gene. The signal peptide can be an immunoglobulin signal peptide or a heterologous signal peptide.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma virus.

In addition to the antibody heavy and/or light chain genes and regulatory sequences, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (DHFR) gene (for use in DHFR-minus host cells with methotrexate selection/amplification), the neo gene (for G418 selection), and glutamine synthetase (GS) in a GS-negative cell line (such as NS0) for selection/amplification.

For expression of the light and/or heavy chains, the expression vector(s) encoding the heavy and/or light chains is introduced into a host cell by standard techniques e.g., electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells, are more likely to assemble and secrete a properly folded and immunologically active antibody. Preferred mammalian host cells for expressing the recombinant antibodies of the invention include Chinese Hamster Ovary (CHO cells), NS0 myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the host cell and/or the culture medium using standard purification methods.

Host cells can also be used to produce portions, or fragments, of intact antibodies, e.g., Fab fragments or scFv molecules by techniques that are conventional. It will be understood by a skilled artisan that variations on the above procedure are within the scope of the present invention. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to myostatin. The molecules expressed from such truncated DNA molecules are also encompassed by the antibodies of the invention.

In a preferred system for recombinant expression of an antibody of the invention, a recombinant expression vector encoding both the antibody heavy chain and the antibody light chain is introduced into CHO cells by e.g., calcium phosphate-mediated transfection. Within the recombinant expression vector, the antibody heavy and light chain genes are each operably linked to enhancer/promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Antibodies, or antigen-binding portions thereof, of the invention can be expressed in an animal (e.g., a mouse) that is transgenic for human immunoglobulin genes (see, e.g., Taylor, et al., *Nucleic Acids Res.* 20:6287-95, 1992).

Uses

Antibodies of the present invention are useful in therapeutic, prophylactic, diagnostic and research applications as described herein. An antibody of the invention may be used to diagnose a disorder or disease associated with the expression of human myostatin. In a similar manner, the antibody of the invention can be used in an assay to monitor myostatin levels in a subject being treated for a myostatin-associated condition.

Therapeutic Uses for the Antibody

Myostatin plays a role in muscle development and a number of related disorders or diseases. In adults, myostatin mRNA is primarily detected in skeletal muscle although lower concentrations are also found in adipose tissue and cardiac tissue (Sharma, M., et al, *J. Cell Physiol.* 180:1, 1999). Myostatin knockout mice have two- to three-fold greater muscle mass than their wild type littermates. The increased muscle mass is the result of fiber hypertrophy and hyperplasia (McPherron, A., et al. *Nature* 387:83-90, 1997 and Zhu, X. et al., *FEBS Letters* 474:71). In addition, the myostatin knockout mice accumulate less fat than their wild type littermates but otherwise appear normal and healthy. Myostatin has also been recently shown to be an important regulator of adipogenesis (Rebbapragada, A., et al., *Mol. and Cell. Bio.* 23:7230-7242, 2003). Additionally, bone structure and content has been recently studied in myostatin deficient mice (Hamrick M. W., et al., *J. Orthopaedic Research* 21:1025, 2003; Hamrick, M. W., et al., *Calcif Tissue Int* 71:63, 2002.

Therefore, a composition comprising an anti-myostatin monoclonal antibody of the invention may be used to increase muscle mass, increase bone density, decrease muscle wasting, or may be useful for the treatment or prevention of conditions wherein the presence of myostatin causes or contributes to undesirable pathological effects or decrease of myostatin levels has a therapeutic benefit in mammals, preferably humans. Preferably a composition comprising an anti-myostatin monoclonal antibody of the invention may be used to increase muscle mass.

Preferably an antibody of the invention may be used in the treatment or prevention of muscle wasting, muscle injury, surgery, repair of damaged muscle, frailty, age-related sarcopenia, disuse atrophy, osteoporosis, osteoarthritis, ligament growth and repair, obesity, suppression of body fat accumulation, obesity, muscular dystrophy of any type, critical care myopathy, alcoholic myopathy, cachexia (e.g., cancer-related or HIV-induced, or resulting from COPD, chronic lung disease, recovery from sepsis, renal failure, liver failure, cardiac failure or disease), metabolic syndrome, post-burn muscle wasting, and Type II diabetes. More preferably, an antibody of the invention may be used in the treatment or prevention of muscle wasting, frailty, age-related sarcopenia, disuse atrophy and cachexia. Most preferably, an antibody of the invention may be used in the treatment or prevention of disuse atrophy or cachexia.

Disuse atrophy may result from numerous causes or incidents including any disorder or disease or state which leads to prolonged immobility or disuse or bed rest including, but not limited to, solid organ transplant, joint replacement, stroke, spinal cord injury, recovery from severe burn, sedentary chronic hemodialysis, post-sepsis recovery and exposure to microgravity. Since myostatin is highly conserved in sequence and function across species, the antibodies of the invention may be used to increase muscle mass, increase bone density or treat or prevent conditions in non-human mammals or avian species [e.g., domestic animals (e.g., canine and feline), sports animals (e.g., equine), food-source animals (e.g., bovine, porcine and ovine), avian species (e.g., chicken, turkey, other game birds or poultry)] wherein the presence of myostatin causes or contributes to undesirable pathological effects or decrease of myostatin levels has a therapeutic benefit.

The use of an anti-myostatin monoclonal antibody of the present invention for treating or preventing of at least one of the aforementioned disorders in which myostatin activity is detrimental or which benefits for decreased levels of bioactive myostatin is contemplated herein. Additionally, the use of an anti-myostatin monoclonal antibody of the present invention for use in the manufacture of a medicament for the treatment of at least one of the aforementioned disorders is contemplated.

As used herein, the terms "treatment", "treating", and the like, refer to obtaining a desired pharmacologic and/or physiologic effect. The effect may be therapeutic in terms of a partial or complete cure for a disease and/or adverse affect attributable to the disease. "Treatment", as used herein, includes administration of a compound of the present invention for treatment of a disease or condition in a mammal, particularly in a human, and includes: (a) inhibiting the disease, i.e., arresting its development; and (c) relieving the disease, i.e., causing regression of the disease or disorder or alleviating symptoms or complications thereof. Dosage regimens may be adjusted to provide the optimum desired response.

As used herein, the term, "preventing" refers to completely or partially preventing a disease or symptom thereof. "Prevention" as used herein, includes administration of a compound of the present invention for prevention the disease from occurring in a subject which may be predisposed to the disease but has not yet been diagnosed as having it.

Composition

An antibody of the invention can be incorporated into pharmaceutical compositions suitable for administration to a subject. The compounds of the invention may be administered alone or in combination with a pharmaceutically acceptable carrier, diluent, and/or excipients, in single or multiple doses. The compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions are designed in accordance with conventional techniques as in e.g., *Remington, The Science and Practice of Pharmacy*, 19$^{th}$ Edition, Gennaro, Ed., Mack Publishing Co., Easton, Pa. 1995 which provides a compendium of formulation techniques as are generally known to practitioners.

A composition of the invention preferably is a "therapeutically effective amount" or a "prophylactically effective amount" of an antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. A therapeutically effective amount is also one in which any toxic or detrimental effect of the antibody, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

A therapeutically-effective or prophylactically-effective amount is at least the minimal dose, but less than a toxic dose, of an active agent which is necessary to impart therapeutic benefit to a subject. Stated another way, a therapeutically-effective amount of an antibody of the invention is an amount which in mammals, preferably humans, increases muscle mass, increases bone density, or treats conditions wherein the presence of myostatin causes or contributes to undesirable pathological effects or decrease in myostatin levels results in a beneficial therapeutic effect in a mammal, preferably a human, including, but not limited to, muscle wasting, muscle injury, surgery frailty, age-related sarcopenia, disuse atrophy, osteoporosis, osteoarthritis, ligament growth and repair, obesity, suppression of body fat accumulation, muscular dystrophy of any type, critical care myopathy, cachexia (e.g., cancer-related or HIV-induced, or resulting from COPD, renal failure, liver failure, cardiac failure or disease), metabolic syndrome and Type II diabetes. Disuse atrophy may result from numerous causes or incidents including any disorder or disease or state which leads to prolonged immobility or disuse or bed rest including, but not limited to, solid organ transplant, joint replacement, stroke, spinal cord injury, recovery from severe burn, sedentary chronic hemodialysis, post-sepsis recovery and exposure to microgravity.

The route of administration of an antibody of the present invention is parenteral. Preferably, the antibodies of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred. Suitable vehicles for such injections are straightforward in the art.

The composition typically must be sterile and stable under the conditions of manufacture and storage in the container provided, including e.g., a sealed vial or syringe. Therefore, compositions may be sterile filtered after making the formulation, or otherwise made microbiologically acceptable. A typical composition for intravenous infusion could have a volume from 20-1000 mL of fluid, such as sterile Ringer's solution, physiological saline, dextrose solution and Hank's solution and a therapeutically effective dose, (e.g., 1 to 1000 mg) of antibody concentration. Dose may vary depending on the type and severity of the disease. As is well known in the medical arts, dosages for any one subject depends upon many factors, including the patient's size, body surface area, age, the particular compound to be administered, sex, time and route of administration, general health, and other drugs being administered concurrently. A typical dose can be, for example, in the range of 1 to 1000 mg; however, doses below or above this exemplary range are envisioned, especially considering the aforementioned factors. A typical dosing regimen may occur daily, weekly, biweekly or monthly. A typical parenteral dosage regimen can be about 10 μg/kg to about 20 mg/kg of total body weight, preferably from about 20 μg/kg to about 10 mg/kg. Progress may be monitored by periodic assessment. For repeated administrations, depending on the condition, the treatment may be repeated until a desired suppression of disease symptoms occurs or desired prevention of disease symptoms occurs. However, other dosage regimens may be useful and are not excluded herefrom.

These suggested amounts of antibody are subject to a great deal of therapeutic discretion. The key factor in selecting an appropriate dose and scheduling is the result obtained. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners.

Therapeutic agents of the invention may be frozen or lyophilized for storage and reconstituted in a suitable sterile carrier prior to use. Lyophilization and reconstitution can lead to varying degrees of antibody activity loss. Dosages may have to be adjusted to compensate. Generally, pH between 6 and 8 is preferred.

Articles of Manufacture.

In another embodiment of the invention, an article of manufacture containing materials useful for the treatment or prevention of the disorders or conditions described above is provided. The article of manufacture comprises a container and a label. Suitable containers include, for example, bottles, vials, syringes, and test tubes. The containers may be formed from a variety of materials such as glass or plastic. The container holds a composition of the invention which is effective for preventing or treating the disorder or condition and may have a sterile access port (for example the container may be an intravenous solution bag or a vial having a stopper pierceable by a hypodermic injection needle). The active agent in the composition is an anti-myostatin antibody of the invention. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

EXAMPLES

Example 1

Identification of a Cleavage Site in Mabs C12 and 510C2

Solutions of antibodies at 1 mg/mL in various buffer conditions (10 mM citrate pH 5, 10 mM citrate pH 6, 10 mM citrate pH 7, and 10 mM citrate/150 mM NaCl pH 7), are incubated at multiple temperatures (−20° C., 4° C., 25° C., and 40° C.) for 4 weeks. Following incubation, samples are characterized by sodium-dodecylsulfate polyacrylamide gel electrophoresis. For antibodies containing the variable domain of C12 or 510C2 (in multiple Fc-isotypes), additional bands, beyond the expected bands for the heavy and light chains of the antibody, are observed. These bands are observed only for samples incubated at pH 7 (with or without NaCl); under sample reducing conditions, two bands are observed, with apparent masses of ~8-10 kDa, and ~12-14 kDa, and under non-reducing conditions, a single band with an apparent mass of ~8-10 kDa is observed. The extent of cleavage, as determined by the relative intensities of these bands appears to be pH dependent (as the bands are less intense at samples incubated at pH 6, and not apparent for samples incubated at pH 5), and temperature dependent. In order to determine the location of cleavage, and to quantitate the extent of cleavage, the same antibody solutions are further characterized by liquid-chromatography/mass spectrometry (LC/MS) and N-terminal sequencing.

Analysis of samples by LC/MS is carried out as follows. For partial reduction of the antibodies, 4 µL of each sample is mixed with 36 µL water. Then, 15 µL of each solution is mixed with 0.5 µL of 3M Tris-HCl buffer, pH 8.0 and 0.5 µL of 50 mg/mL DTT and 45 µL of water. Both solutions of each sample are analyzed by LC/MS. For antibody deglycosylation, 3 µL of each sample is mixed with 60 µL of water, 1.0 µL of 3M tris-HCl buffer, pH 8.0 and 1.0 µL of PNGase F solution (PROZYME®, 1 U/mL). The solutions are incubated at 37° C. for 6 hrs and then analyzed by LC/MS. For complete trypsin digestion, 20 µL of each sample is lyophilized to dryness under speed-vacuum system and then reconstituted in 4.5 µl of 7 M guanidine-HCl, 0.4 M tris-HCl buffer, pH 8.0 and 0.5 µL of 50 mg/mL DTT solution. The solutions are incubated at 37° C. for 40 min and then diluted with 95 µL water. Each solution is treated with 2.0 µL of 0.5 mg/mL porcine trypsin at 37° C. for 3 hrs. The solutions are acidified with acetic acid and then analyzed by LC/MS or LC/MS/MS. The intact, partially reduced, and deglycosylated samples are analyzed using a Waters HPLC/LCT premier or Q-TOF micro mass spectrometer. HPLC and mass spectrometer parameter setting are adjusted based on samples and requirements.

The deconvoluted mass spectra for the C12 antibody, incubated at pH 7, and 40° C. for four weeks, exhibits two peaks, with masses at 134894 and 145116 Da. The mass difference is about 10220 Da between them, which matches the expected residue mass of the N-terminal peptide 1-93 (expected: 10221.4 Da) of the light chain. This result is confirmed by LC/MS analysis for the partial reduction samples. In this sample, three masses are detected; 23312.7, 13091.3 and 10239.4 Da, which are consistent with the intact light chain 1-219 (expected: 23313.1 Da), the C-terminal peptide 94-219 (expected: 13091.6 Da) and N-terminal peptide 1-93 (expected: 10239.4 Da) of the light chain. Essentially identical results are obtained with the 510C2 antibody as well, although the relative amount of cleavage products is lower for this antibody. Table 1 summarizes the percentage of cleaved light chain determined for the analysis of the partially reduced samples.

N-terminal sequencing is also used to characterize the incubated samples. Automated Edman Degradation amino acid sequence analysis is performed on samples applied to a PROSORB® sample preparation cartridge utilizing Applied Biosystem Inc. (ABI) gas phase (GP-PVDF) method. Each residue is analyzed on a sphere-5 PTH 220x 2.1 mm ABI BROWNLEE® column at 55° C. with a flow rate of 325 µL/minute. Data is analyzed utilizing ABI's Model 610A data analysis program. For antibody samples incubated at 40° C., two sequences are observed; for C12, the two sequences observed are "DIQMTQ" (SEQ ID NO: 34) which corresponds to the expected N-terminus of the C12 light chain, and "PLTFGG" (SEQ ID NO: 35) which corresponds to residues 94-99 of the C12 light chain. Identical results are obtained for analysis of incubated 510C2 antibody solutions. Using the relative amounts of each sequence, the extent of cleaved product is calculated, and is summarized in Table 1.

TABLE 1

Summary of cleavage extent at the Asn93-Pro94 peptide bond

| | % Cleaved (pH 7, 4 wks, 40° C.) | |
| --- | --- | --- |
| Mab | LC/MS | N-terminal Seq. |
| C12-IgG4 | 22% | 15-20% |
| C12-IgG1 | 21% | 20-22% |
| C12-IgG2 | 14% | 5-10% |
| 510C2-IgG4 | 3% | 5-8% |
| 510C2-IgG1 | 5% | 5-9% |

Example 2

Removal of the Chemical Cleavage Site in the C12 and 510C2 Antibodies

To remove the cleavage site in C12 and 510C2, single amino acid substitutions of each individual amino acid are used to replace the asparagine residue in CDRL3 of both monoclonal antibodies. ELISA is used to determine the effects of the individual amino acid substitutions on affinity to myostatin compared to C12 or 510C2 Fabs.

ELISA plates are coated with myostatin diluted to 4 ug/ml in carbonate buffer (50 mM NaHCO$_3$ pH 8.3) and 50 μL added per well. Plates are covered with sealing tape and incubate overnight at 4° C. Thereafter, plates (Greiner U-bottom plates Cat #650061) are washed three times with PBS-T (0.1% Tween-20) using an automatic plate washer. 200 μL of blocking buffer (PBS+1% BSA+0.1% Tween-20) is added to every well and incubated at room temperature for one hour. Plates are washed and 50 μl of sample added per well. Samples are composed of periprep Fabs diluted in PBST/BSA starting at a 1:3 dilution and then serially diluted in half-log steps. Plates are washed and 50 μL of secondary antibody solution (1:2000 goat anti-human-kappa-AP Southern Biotech Cat # 2060-04 in PBST/BSA) is added to every well. Following an additional wash step, 100 μL of AP substrate is added per well and incubates at room temperature for about 10 minutes. The absorbance or OD at 560 nm is read. C12 or 510C2 is included on each ELISA plate as an affinity reference standard. The concentration of Fabs is determined by a quantitative ELISA using an anti-Fd antibody (Sheep anti-Fd Biodesign) to capture protein and goat anti-human-kappa-AP (Southern Biotech) to detect. A purified Fab standard is run on each plate to generate a standard curve for the concentration determinations.

Modified Fabs derived from C12 and 510C2, in which the Asn residue in the CDRL3 is replaced with H or R in C12, or H, S, T, or A in 510C2, maintain affinity to myostatin similar to that of the parent Fab as determined by ELISA. Each of these substitutions yields ELISA affinity curves similar to the respective parent Fab control as determined by similar absorbance readings at the same concentration of Fab (see FIG. 4). However, if the asparagine residue in the CDRL3 is replaced with valine, proline, glycine, glutamine, tryptophan, tyrosin, cysteine, leucine, isoleucine, methionine, phenylalanine, threionine, serine, lysine, alaine, aspartic acid, or glutamic acid in C12, or arginine, aspartic acid, cysteine, glutamic acid, glutamine, glycine, isoleucine, leucine, lysine, methionine, phenylalanine, tyrosin, valine, tryptophan, or proline in 510C2, each of these substitutions reduces the binding affinity of the modified Fabs to myostatin as compared to that of the parent Fab. Moreover, attempts on the modification of the Pro residue of the dipeptide Asn-Pro failed because all the substitutions reduce the binding affinity of the modified Fabs to myostatin as compared to that of the parent Fab.

Example 3

Comparison of Cleavage Between the C12 Antibody, and the Variant LC-N93H

Solutions of antibodies at 1 mg/mL in 10 mM phosphate, pH 7.4/150 mM NaCl, are incubated at multiple temperatures (4° C., 25° C., and 40° C.) for 4 weeks. Following incubation, samples are characterized by sodium-dodecylsulfate polyacrylamide gel electrophoresis and N-terminal sequencing as described above. Under these conditions, additional bands are observed by SDS-PAGE for the C12 antibody sample incubated at 40° C. beyond the expected bands for the heavy and light chains of the antibody; the observed bands migrate at ~8 kDa under non-reducing conditions, and ~8 kDa and ~14 kDa under reducing conditions. In contrast, no additional bands are seen for the LC-N93H variant. N-terminal sequencing of the incubated samples confirms that cleavage between Asn93 and Pro94 in the light chain occurs in the C12 antibody sample, with ~10-20% of the sequence corresponding to the new N-terminus (PLTFGG (SEQ ID NO: 35)), whereas there is no additional light chain sequence other than the expected N-terminus for the LC-N93H variant.

Example 4

Myostatin/SBE Reporter Assay

In this reporter assay, a plasmid encoding a luciferase gene downstream of a SMAD binding element ("SBE-luciferase"), more specifically (CAGA)$_{12}$, expresses luciferase protein when a molecule such as myostatin, GDF-11, or other TGF-β superfamily member binds its own receptor, thereby triggering SMAD signaling which results in a phosphorylated SMAD complex which is capable of binding the SBE. The CAGA sequence is a TGF-β responsive sequence within the promoter of the TGF-β induced gene PAI-1 (Denner et al., EMBO J., 17:3091-3100, 1998). To generate the plasmid, the SBE repeat sequence: tcgagagccagacaaaaagccagacatt-tagccagacactcgagag ccagacaaaaagccagacatttagcca-gacactcgagagccagacaaaaagccagacatttagccagacactcgaga gccagacaaaaagccagacatttagcca-gacactcgagagccagacaaaaagccagacatttagccagacac (SEQ ID NO: 36) is cloned into the NheI-HindIII site of the pGL3-basic vector (Promega #E1751). This plasmid is used for transient transfections into HEK293 EBNA cells.

The quantity of light measured is proportional to the quantity of luciferase produced, which is proportional to the amount of myostatin to which the cells are exposed. The presence of an inhibitor (e.g., an antibody that binds myostatin) reduces the quantity of myostatin able to activate the SBE which ultimately results in a reduced production of light.

In this assay, HEK293 EBNA cells (Edge Biosystems) in DMEM/F12 media (3:1) (Gibco 93-0152DK), 10% FBS, 20 mM Hepes, 4 mM L-glutamine ("Complete Medium") are seeded at about 25000 cells per well in poly-lysine coated inner wells of a 96-well plate (BD Biocoat 35-4461) and incubated overnight at 37° C. The following day, the cells are washed in PBS and 50 μl OptiMEM I (Gibco 31985-070) is added per well. The cells are transfected with 50 μl of the following SBE-luciferase DNA mixture: 80 μl Lipofectamine (Gibco 11668-019 combined with 1.5 ml OptiMEM and allowed to sit for 5 minutes then added to a tube in which 20 μg SBE-luciferase DNA is combined with 1.5 ml OptiMEM and 200 μL Plus reagent, (Invitrogen), mixed and allowed to sit for 5 minutes. After the two mixtures are added together, the solution is mixed vigorously and allowed to stand for 30 minutes before 50 μL of this solution ("transfection media") is added to each well. The cells are then incubated overnight at 37° C. in 5% CO$_2$. For each plate of cells, myostatin (R&D Systems 788-G8) is diluted to 20 ng/ml in complete medium. Each antibody of the invention to be tested is titrated in Complete Medium, e.g., from about 40 μg/ml to about 50 ng/ml. The transfection media are removed from the wells and 50 μL of an antibody dilution is added per well and 50 mL of GDF-8 (myostatin) or GDF-11 (R&D Systems) is added per well. The plate of cells is then incubated overnight at 37° C. in 5% CO$_2$. The following day, the media are aspirated, the cells are washed in PBS and 75 μL lysis buffer (Promega E266A) is added. The luciferase activity in the cell lysate is measured using Luciferase Reagent according to manufacturer's instructions (Promega E2620). Luminescence is plotted against Log$_{10}$ Mab concentration (μg/ml) and the IC$_{50}$ for each Mab for myostatin and GDF-11 is calculated.

Mab C12 and a modified monoclonal antibody derived C12 (C12-N93H) when tested in these conditions with myostatin yield IC$_{50}$ values about 9.59 nM and 7.03 nM respectively. Neither C12 nor C12-N93H demonstrates neutralization activity in this assay when tested with GDF-11 instead of myostatin, indicating that the modified antibody like its parent antibody preferentially binds myostatin over GDF-11.

What we claim is:

1. An anti-myostatin monoclonal antibody comprising a heavy chain variable region (HCVR) and a light chain variable region (LCVR), wherein said HCVR comprises:
   a) a peptide at CDRH1 with a sequence as shown in SEQ ID NO: 23,
   b) a peptide at CDRH2 with a sequence as shown in SEQ ID NO: 25,
   c) a peptide at CDRH3 with a sequence as shown in SEQ ID NO: 27, and wherein said LCVR comprises:
   a) a peptide at CDRL1 with a sequence as shown in SEQ ID NO: 13,
   b) a peptide at CDRL2 with a sequence as shown in SEQ ID NO: 14, and
   c) a peptide at CDRL3 with a sequence selected from the group consisting of SEQ ID NO: 16, 17, 18 and 19.

2. The monoclonal antibody of claim 1, wherein the framework regions of the HCVR and LCVR are human framework regions.

3. The monoclonal antibody of claim 1, wherein the HCVR comprises a sequence as shown in SEQ ID NO: 11 and the LCVR comprises a sequence selected from the group consisting of SEQ ID NO: 4, 5, 6 and 7.

4. A pharmaceutical composition comprising an antibody of claim 1 and a pharmaceutically acceptable carrier.

5. A pharmaceutical composition comprising an antibody of claim 3 and a pharmaceutically acceptable carrier.

6. A method of treating muscle wasting, frailty, age-related sarcopenia, disuse atrophy and cachexia in a subject in need thereof by administering a therapeutically effective amount of a monoclonal antibody of claim 1.

7. An anti-myostatin monoclonal antibody comprising a HCVR and a LCVR, wherein said HCVR comprises:
   a) a peptide at CDRH1 with a sequence as shown in SEQ ID NO: 24,
   b) a peptide at CDRH2 with a sequence as shown in SEQ ID NO: 26,
   c) a peptide at CDRH3 with a sequence as shown in SEQ ID NO: 28,
   and wherein said LCVR comprises:
   a) a peptide at CDRL1 with a sequence as shown in SEQ ID NO: 13,
   b) a peptide at CDRL2 with a sequence as shown in SEQ ID NO: 14, and
   c) a peptide at CDRL3 with a sequence selected from the group consisting of SEQ ID NO: 21 and 22.

8. The monoclonal antibody of claim 7, wherein the framework regions of the HCVR and LCVR are human framework regions.

9. The monoclonal antibody of claim 7, wherein the HCVR comprises a sequence as shown in SEQ ID NO: 12 and the LCVR comprises a sequence selected from the group consisting of SEQ ID NO: 9 and 10.

10. An anti-myostatin monoclonal antibody comprising a light chain with a sequence as shown in SEQ ID NO: 32 and a heavy chain with a sequence as shown in SEQ ID NO: 33.

11. A pharmaceutical composition comprising an antibody of claim 7 and a pharmaceutically acceptable carrier.

12. A pharmaceutical composition comprising an antibody of claim 9 and a pharmaceutically acceptable carrier.

13. A method of treating muscle wasting, frailty, age-related sarcopenia, disuse atrophy and cachexia in a subject in need thereof by administering a therapeutically effective amount of a monoclonal antibody of claim 7.

14. A method of treating muscle wasting, frailty, age-related sarcopenia, disuse atrophy and cachexia in a subject in need thereof by administering a therapeutically effective amount of a monoclonal antibody of claim 9.

* * * * *